United States Patent [19]

Benkovic et al.

[11] Patent Number: 4,521,509
[45] Date of Patent: Jun. 4, 1985

[54] METHOD FOR DEGRADING DNA

[75] Inventors: Stephen J. Benkovic, State College, Pa.; Scott D. Putney, Brigaton; Paul R. Schimmel, Lexington, both of Mass.

[73] Assignee: Research Corporation, New York, N.Y.

[21] Appl. No.: 444,304

[22] Filed: Nov. 24, 1982

[51] Int. Cl.³ .................. C12Q 1/68; C12P 19/34; C12N 15/00; C12N 1/00; G01N 31/14; C07H 21/02; C07H 21/04

[52] U.S. Cl. .................. 435/6; 435/91; 435/172.3; 435/317; 436/63; 436/94; 536/27; 935/17; 935/19; 935/77

[58] Field of Search .................. 435/91, 172.3, 317.6, 435/196, 199; 436/63, 94; 536/27, 28, 29

[56] References Cited

PUBLICATIONS

Bryant et al.: Phosphorus Chem. Directed Biol. Lect. Int. Symp., Stec (ed.), Pergamon Press, New York (1979), pp. 129–131.
Green et al.: Proc. Natl. Acad. Sci. USA 77, 2455 (1980).
Weaver et al.: Nucleic Acids. Res. 7, 1175 (1979).
Green et al.: Proc. Natl. Acad. Sci. USA, 77, 2455 (1980).
Weaver et al.: Nucleic Acids. Res., 7, 1175 (1979).
Kunkel et al., Proc. Natl. Acad. Sci., 78, 6734 (1981).
Bryant et al., Chem. Abstr., 94, 26753p (1981) of Phosphorus Chem. Directed Biol. Lect. Int. Symp., 1979, Stec (ed.), Pergamon, New York, pp. 129–131.
Shalloway et al., Cell 20, 411 (1980).
Orr, George A., et al., "Adenosine 5'-O-([γ-$^{18}$O-]γ-thio) Triphosphate Chiral at the γ-phosphorus: Stereochemical Consequence of Reactions Catalyzed by Pyruvate Kinase, Glycerol Kinase, and Hexokinase", Proc. Natl. Acad. Sci., USA, vol. 75, No. 5, pp. 2230–2233, May 1978.
Kwan-Fu Rex Sheu, Frey, Perry A., "UDP-glucose Pyrophosphorylase", Stereochemical Course of the Reaction of Glucose 1-phosphate with Uridine-5'[1--thiotriphosphate] (1978) J. Biol. Chem., 253, 3378.
Atkinson, Maurice R., et al., "Enzymatic Synthesis of Deoxyribonucleic Acid XXXIV Termination of Chain Growth by a 2',3'-Dideoxyribonucleotide" (1969) Biochemistry 8, 4897–4904.
Sanger, F., Nicklen, S., Coulson, A. R.; "DNA Sequencing with Chain-Terminating Inhibitors", Proc. Natl. Acad. Sci., USA, vol. 74, pp. 5463–5467, Dec. 1977.
Putney, Scott D.; Benkovic, Stephen J., Schimmel, Paul R.; "A DNA Fragment with an α-phosphorothioate Nucleotide at One End is Asymmetrically Blocked from Digestion by Exonuclease III and can be Replicated In Vivo", Proc. Natl. Acad. Sci. USA, vol. 78, pp. 7350–7354, Dec. 1981.

(List continued on next page.)

Primary Examiner—Thomas G. Wiseman
Assistant Examiner—James Martinell
Attorney, Agent, or Firm—Scully, Scott, Murphy & Presser

[57] ABSTRACT

2'-deoxyadenosine 5'-0-(1-thiotriphosphate) (dATP(α-S)) was introduced into the 3'-ends of DNA restriction fragments with E. coli DNA polymerase I to give phosphorothioate internucleotide linkages. Such "capped" 3'-ends were found to be resistant to exonuclease III digestion. Moreover, the resistance to digestion is great enough that, under the conditions employed, just one strand of a double helix was digested by exonuclease III when "cap" was placed at only one end; when digestion was carried to completion, the production of intact single strands resulted. When digestion with exonuclease III was limited, and followed by S1 nuclease treatment, double stranded DNA fragments asymmetrically shortened from just one side were produced. In this way thousands of nucleotides can be selectively removed from one end of a restriction fragment. In vitro introduction of phosphorothioate linkages into one end of linearized replicative plasmid, followed by exonuclease III and S1 nuclease treatments, gave rise to truncated forms which, upon circularization by blunt end ligation, transformed E. coli and replicated in vivo.

28 Claims, 8 Drawing Figures

PUBLICATIONS

Burgers, Peter M. J., Eckstein, Fritz, "A Study of the Mechanism of DNA Polymerase I From *Escherichia coli* with Diastereomeric Phosphorothioate Analogs of Deoxyadenosine Triphosphate" (1979) *J. Biol. Chem.*, 254, 6889.

Bryant, Floyd R., Benkovic, Stephen; "Stereochemical Course of the Reaction Catalyzed by 5'-Nucleotide Phosphodiesterase from Snake Venom" (1979) *Am. Chem. Soc.*, p. 2825.

Eckstein, F., Armstrond, V. W., Steinbach, H.; "Stereochemistry of Polymerization by DNA-dependent RNA-polymerase from *Escherichia coli*: An Investigation with a Diastereomeric ATP-analogue", *Proc. Natl. Acad. Sci.*, USA, vol. 73, No. 9, pp. 2987-2990, Sep. 1976.

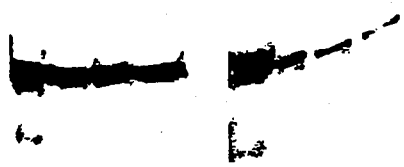
FIG.IB

METHOD FOR DEGRADING DNA

FIELD OF THE INVENTION

This invention relates to the field of molecular biology and particularly to the art of recombinant DNA technology. More specifically, the invention relates to a method by which double stranded DNA molecules may be shortened asymmetrically, as well as to a method by which single stranded molecules may be obtained from double stranded DNA.

BACKGROUND OF THE INVENTION

As is now well known, deoxyribonucleic acid (DNA) exists as a long unbranched molecule consisting of many similar units known as *nucleotides*. The individual nucleotides are arranged into two large polymeric chains which are interwound to form the so-called double helical structure of DNA. The DNA nucleotides are generally of four types characterized by possessing one of four organic heterocyclic ring moieties often referred to as bases. Two of the bases adenine (A) and guanine (G) belong to the class of heterocyclic ring compounds known as purines while the other two bases thymine (T) and cytosine(C) belong to the pyrimidine class of heterocyclic rings. In addition to a base, each nucleotide contains a five carbon sugar (pentose) called deoxyribose and a phosphate ($PO_4$) group.

A part of one chain of DNA may be represented by the structure:

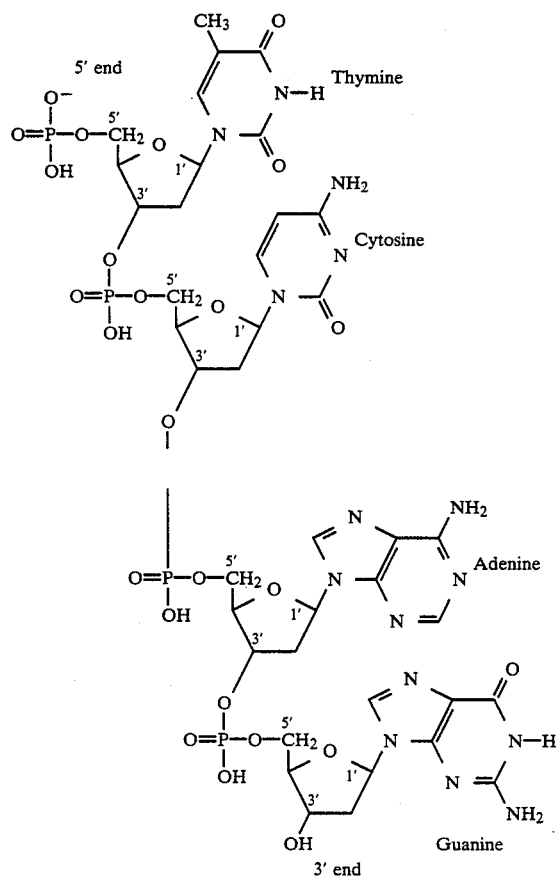

By convention the carbon atoms which comprises the deoxyribose moiety are given designations 1' to 5'. The polymer is formed through diester linkages of the phosphate group to the 3' and 5' carbon atoms of adjacent pentose residues. This configuration results in the chain possessing a free phosphate group at the 5' terminus and a free OH group at its 3' terminus. Because of this arrangement of atoms the polynucleotide chain is said to have *polarity*, that is one end of the molecule is distinguishable from the other, much as the two ends of a bar magnet would be distinguishable.

In its native form, DNA is comprised of two polynucleotide chains arranged such that the bases of the two chains are oriented towards the center of the molecule and the sugar-phosphate groups oriented to the outside of the molecule.

More specifically, the bases are oriented in a complementary fashion so that the specific purine G is always opposite the specific pyrimidine C and the specific purine A is always opposite a specific pyrimidine T. Each A=T or G≡C base pair is stabilized by two and three hydrogen bonds respectively. The sugar-phosphate groups, often referred to as the "backbone" of the molecule are arranged in an antiparallel fashion, that is to say if one chain is oriented 5'→3' to other chain is oriented 3'→5'. This specific arrangement is illustrated as follows:

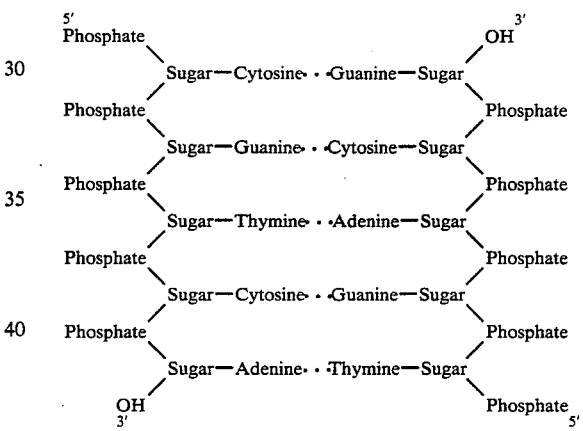

As mentioned above in its native form DNA exists as a double helix; this is the consequence of the fact that each base pair is displaced slightly (~36°) in axial rotation from the base pair adjacent to it. The molecule thus makes one complete spiral turn every ten base pairs resulting in the well-known double helical structure shown in FIG. 6.

DNA molecules are large, chemically stable and easily replicated and as such are ideally suited to function as the storage form of genetic information. For example, most of the genetic repertoire of the bacteria *E. coli* is contained within a single DNA molecule composed of approximately $4.2 \times 10^6$ nucleotide base pairs.

The flow of genetic information in cells is well known. The information directing the biosynthesis of any protein is encoded in the sequences of DNA nucleotides known as a gene.

Transcription is the process by which the retrieval of information is begun. Transcription involves the resynthesis of the information in the form of another type of nucleic acid called ribonucleic acid (RNA). One type of RNA, messenger RNA (mRNA), transports the information to the site of protein synthesis called a ribosome.

Once the mRNA is synthesized from the gene, the process of protein synthesis may begin. This process is essentially one of molecular decoding, in which the nucleotide sequence of the mRNA provides a template for the synthesis of a particular protein. Since there is a change from a nucleic acid language into that of a protein language, this process of protein synthesis appropriately is referred to as translation. Continuing the analogy a bit further, it would be appropriate to think of the constituents of the nucleic acids, the nucleotides, as representing the alphabet of the nucleic acid language and the amino acids, the building blocks of proteins, as representing the alphabet of the protein language. During the process of translation not only are the languages changing but the alphabets are changing as well. This is a particularly complex process which is known to involve over 100 types of molecules. As the mRNA is passed through the ribosome (much like the tape through a tape recorder) groups of 3 nucleotides (codons) are positioned such as to orient accessory RNA molecules, known as transfer RNA (tRNA), carrying a single amino acid into the proper alignment for the addition of the amino acid to the growing protein chain.

Of special interest with respect to the subject invention is the relationship of the structure and function of DNA has to the application of recombinant DNA (genetic engineering) technology.

One of the main objectives of genetic engineering experiments is to provide to a recipient organism a source of genetic information which will permit the recipient organism to perform a new function. Generally, this is accomplished by providing the genetic information in the form of a piece of DNA which has been isolated from another organism and chemically integrated into the DNA which normally exists within the recipient organism. The result of such a procedure is a molecular hybrid and is often referred to as a chimeric DNA molecule (Chimera - Gk. mythol.—A fire breathing monster usually represented as a composite of a lion, a goat and a serpent.). Since the chimeric molecule is often replicated (i.e. found in multiple copies) within the recipient organism, the DNA is said to have been cloned. The construction of stable, functioning genetic chimeras by means of genetic engineering techniques, involves a series of in vitro and in vivo steps.

The source of DNA to be cloned may include viruses, bacteria, fungi, plants or animals. This DNA is generally referred to as donor DNA and contains the desired genetic information to be propagated. This DNA represents one component of the chimera.

The other component of the chimera, the vector, is a segment of DNA into which the donor DNA is integrated. This vector DNA, also referred to as the cloning vehicle, is a segment of non-chromosomal DNA that is capable of independent replication when placed within a microbe. The cloning vehicles commonly used are derived from viruses, bacteria, fungi, plants or a combination thereof.

For example, an early step in the genetic engineering process involves integrating a fragment of donor DNA containing the desired genetic information into an appropriate vector. Generally, this involves treating both the vector DNA and the donor DNA with an enzyme (a restriction endonuclease) which cleaves only at specific sites within the two DNAs. Since the termini of the cleaved molecules are complementary, due to the action of the restriction enzyme, the foreign DNA may be integrated at a particular point within the plasmid. Optionally, this site of integration itself will have been previously "engineered" so as to be nearby the appropriate control sequences which will ensure the successful expression (i.e. transcription and translation) of the integrated DNA. The last step in the integration involves the enzymatic sealing of the phosphodiester backbone of the DNA molecule employing the enzyme DNA ligase.

During the course of some recombinant DNA experiments, it is necessary to generate a single stranded DNA molecule from a double stranded DNA molecule. In addition it is often desirable to asymmetrically decrease the length of a double stranded molecule in a progressive, controlled manner. The instant invention provides a rapid and generally applicable method to perform either of these manipulations.

BRIEF DESCRIPTION OF THE INVENTION

As mentioned above, DNA normally exists as a double stranded helix where the two strands are arranged in an antiparallel fashion. Each strand contains information complementary to that of the other. The current method used to generate single strands is to separate the two strands with chemicals and heat, and to isolate the two single strands by electrophoresis through a porous matrix. This technique, called electrophorectic strand separation, is time consuming (requiring an entire day or more), often gives poor recovery of the single strands, is ineffective for many DNA molecules, and often leaves contaminants with the DNA which hinder subsequent experiments. Another method for generating single strands calls for cloning the DNA into a single stranded bacterial virus, called M13, which contains only one strand of the DNA. Although this method is useful for very specialized applications, such as DNA sequencing, it is time consuming to clone the DNA into M13 (taking several days or more) and the DNA of interest is always attached to viral DNA. For these reasons, M13 is not used to generate single strands for most applications.

The subject invention provides a rapid, generally applicable method to generate single strands from double stranded DNA by removing nucleotides from only one end of the molecule. The technique calls for placing a derivative of a normal component of DNA at one 3′ end of a double stranded DNA molecule. The derivative, an α-phosphorothioate nucleotide (denoted as dNTPαS) has a sulfur substituted for an oxygen at the α-phosphorus. A widely used commercially available enzyme, DNA polymerase, will insert the dNTPαS into the 3′ side of one end of a double stranded DNA molecule, as long as that end has a recessed 3′ terminus. Recessed termini result because the strands at the end of the DNA molecule are not of equal length, when the 5′ strand overlaps the 3′ strand, the 3′ strand is said to be recessed. Alternatively the 3′ strand may overlap resulting in a recessed 5′ terminus. The ends can be made such that only one of the strands is recessed at the 3′ terminus by generating the ends with the appropriate restriction endonucleases, (enzymes commonly used for recombinant DNA manipulations). Because there are many restriction enzymes with different sequence specificities currently available, the election of a specific one to give a 3′ recessed terminus would be a matter to be practiced by an art skilled worker.

By no means exhaustive, examples of restriction endonuclease which generate recessed 3′ termini by recognizing defined sequences with double stranded DNA include: Ava I, Ava II, Bam HI, Bcl I, Bgl II, Bst EII, Dde I, Eco RI, Eco RII, Hind III, Hinf I, Hpa II, Mbo I, Sal I, Sau 3A, Sau 96I, Taq I, Xba I, and Xho I. This activity is in constrast to other restriction endonucleases which result in 5' recessed termini, such as Bgl I, Cfo I, Dpn I, Hae III, Hha I, Kpn I, Pst I, Pvu I, Sph I, Sst I, Sst II, and Xor II; or flush-ended termini such as Alu I, Bal I, Hae III, Hpa I, Mbo II, Pvu II, Sma I and Tha I.

Once the dNTPα-S is situated at one of the 3' ends, treatment of the DNA with exonuclease III (another widely used enzyme) will result in 3' endwise degradation of the DNA from the side not containing a dNTPα-S. In other words, the dNTP S protects the DNA from digestion with exonuclease III, and if digestion is allowed to proceed to completion, a single strand will be generated. Such a digestion takes on the order of minutes to complete depending on the length of the DNA fragment.

Alternatively, exonuclease III can be stopped before it reaches the end of the DNA resulting in a partially single stranded/double stranded molecule. Using another enzyme, S1 nuclease, which digests exclusively single strands, the remaining single strand can be removed. In this way the length of the DNA can be decreased by digestion from only one end, that is asymmetrically. Other methods of decreasing the length of double stranded DNA use enzymes or combinations of enzymes which degrade both ends of the molecule simultaneously. These methods are, therefore, unsuitable if one end of the molecule is required intact.

Advantages of the dNTPα-S method are that it is rapid, is effective for DNAs of all lengths and sequences, results in yields of essentially 100%, and does not contaminate the DNA. It is a superior way to either generate single stranded DNA from double strands or to asymmetrically shorten double stranded DNA. An important attribute of the dNTPαS is that they allow the DNA which contains them to be introduced directly into cells because the analogs do not interfere with the enzymes the cells use to replicate their DNA.

DETAILED DESCRIPTION OF THE DRAWINGS

FIG. 1b represents an electrophoretic gel pattern of fragments of DNA resulting from the treatment of Exonuclease III upon dAMPαS containing and non-containing DNA molecules.

FIG. 8A illustrates the specificity of endonuclease Dde I.

FIG. 8B illustrates an S fragment after treatment with DNA polymerase I.

DETAILED DESCRIPTION OF THE INVENTION

Figure 1A:
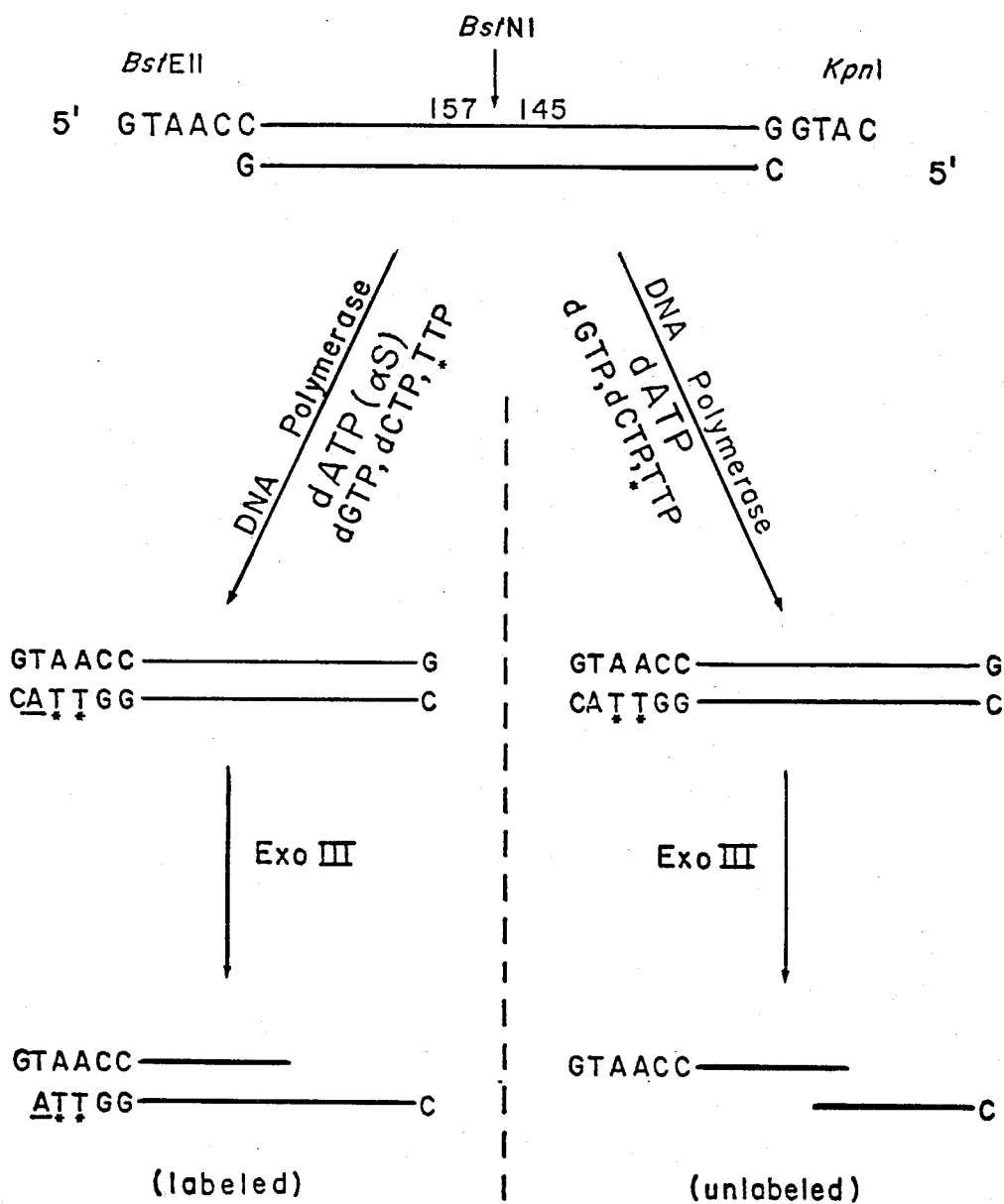
FIG. 1a illustrates the sequential action of DNA polymerase I and Exonuclease III on a fragment of DNA. The phosphorus of the dTTP that was radioactively labelled is indicated by an asterisk and the dAMPαS is indicated by an underline.

During the polymerization of DNA single nucleotide subunits are added to the existing DNA chain. The reaction can be represented by the formula:

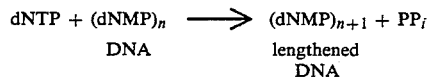

where $(dNMP)_n$ represents DNA, a polymer of dexoyribonucleoside monophosphates of length n and $PP_i$ represents pyrophosphate. The above reaction is well-known and has been shown to be catalyzed both in vivo and in vitro by an enzyme known as DNA-dependent DNA polymerase. In the bacterium *E. coli,* this enzyme is referred to as DNA polymerase I.

The demonstration of DNA polymerase activity in vitro, was very useful in that it allowed for manipulation of experimental parameters such as changes in reactant concentrations, salt and pH. Additionally, analogs of the natural nucleoside triphosphates could be tested for the effect on stimulation, or inhibition of DNA synthesis as well as to elucidate the stereochemistry of the reaction mechanism.

Of particular interest with respect to the subject invention, are the diastereomeric phosphorothioate analogs of the nucleoside triphosphates specifically $S_p$ diasteromer of the deoxyribonucleoside thiotriphosphate (dNTPαS) in which a sulfur atom is substituted for an oxygen atom at the alpha phosphate. The structure of the analog and the unmodified nucleotides are as follows:

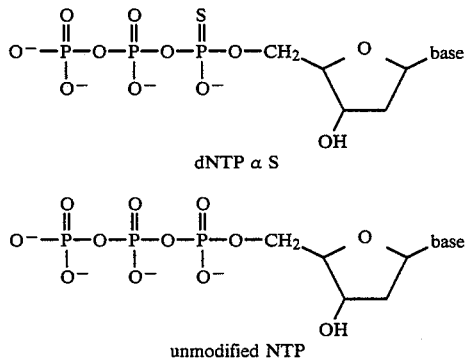

It has been shown (P. M. J. Burgers and F. Eckstein J. Biol. Chem. 254(15):6889–93) that said analogs act as substrates for the *E. coli,* DNA polymerase I and are incorporated into growing DNA chains at an efficiency similar to that of the unmodified substrates.

Although the polymerization activity is apparently unaffected, quite unexpectedly it has been found, as disclosed herein, that the activity of certain nucleases (depolymerizing enzymes) are inhibited by said analogs.

Deoxyribonucleases (DNases) are DNA degrading enzymes and can be categorized into two broad classes: exonucleases or endonucleases. As the names imply exonucleases degrade DNA from the ends of the polymer. Certain exonuclease exhibit a polarity of degradation activity, that is some enzymes degrade from the 3' end of a strand to the 5' end, while others degrade 5' to 3' and still other degrade both 5' and 3' ends simultaneously. Endonucleases degrade DNA by causing strand breaks to occur in the middle of a DNA molecule usually at specific nucleotide sequences. Among this class are the well-known restriction endonucleases which are so useful in recombinant DNA experiments. In addition to the location and polarity of degradation, nuclease are also distinguishable in their ability to degrade double stranded or single stranded DNA. Some of these activities, as they relate to the subject invention, will be discussed in detail below.

According to one embodiment of the invention, full length single stranded DNA may be generated from a double-stranded template owing to the differential effects of said analogs on the activity of various nucleases. Exonuclease III degrades double stranded DNA specifically from the 3' ends of the strands and is inactive against DNA containing dNTP[αS] analogs (See Example I). To obtain an intact single stranded molecule from a double stranded DNA sample, the analog must be incorporated into one strand of the DNA but not the other. This differential affect is accomplished because of the unique requirements of the enzyme used to incorporate the analog into the DNA.

Figure 7:
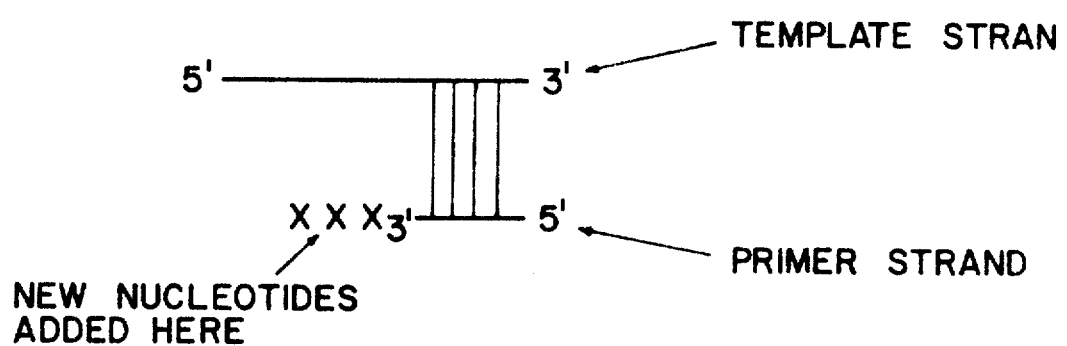
FIG. 7 illustrates the active substrate of DNA polymerase.

The enzyme used to incorporate the dNTPαS base is DNA polymerase I. As mentioned above this enzyme will add nucleotides (both normal and the analogs) to an existing piece of DNA. However the DNA must possess several structure features in order to serve as a substrate for the enzyme. One strand of the DNA must possess a free 3' OH group into which the incoming nucleotide is attached; this is referred to as the primer strand. Additionally the opposite strand must extend past the primer thus serving as a template directing the insertion of a particular nucleotides according to the base pairing rules described above. The active substrate, a 3' recessed terminus, would have a configuration such as shown in FIG. 7.

This type of configuration is easily generated, as is well-known in the art, by the action of some of the restriction enconucleases described above. For example the endonuclease Dde I (isolated from *Desulfovibrio desulfuricans*) possess the specificity shown in FIG. 8A.

After treatment with DNA polymerase I employing dCTP, dGTP, dTTP and dATPαS the fragment would appear as shown in FIG. 8B and, whereupon after treatment with Exonuclease III the unprotected 3' strand will be degraded and the protected strand will not be subject to the action of the exonuclease.

It will be obvious to those skilled in the art that the opposite end of the molecule would possess the same configuration resulting from the action of Dde I at the adjacent site. It is therefore preferable to generate the fragments using two restriction enzymes one such as Dde I which generates 3' recessed termini and one other enzyme such as PvuI which would generate 5' recessed termini or PvuII which generates blunt ends and thus would not form appropriate primers or templates for DNA polymerase I. The selection of the appropriate combination, from the over 200 known endonucleases, would depend on the specific parameters of the operation as would be determined by the skilled artisan.

In another embodiment of the subject invention, the exonuclease III can be stopped prior to complete digestion of the unprotected strands thus yielding a double stranded DNA molecule with a single stranded "tail". The single stranded portion may then be removed by the action of yet another nuclease, S1, which is specific for single-stranded DNA. Employing this feature of the invention the skilled artisan can effect a controlled degradation DNA from one end of the molecule. (i.e. asymmetric degradation)

The NTP thio analogs have been used extensively as tools for analysis of the stereochemistry of enzyme mechanisms. For example, the mechanisms of polymerase, kinases, exonucleases, and of nucleotidyl tranferases have been explored with these compounds. Their significance for such studies is that the stereochemistry of the reaction about the chiral phosphorus atom can easily be determined. We disclose herein the utility of the NTP(αS)'s for certain aspects of in vitro modification of DNA, with emphasis on their potential as aids to recombinant DNA manipulations. Surprisingly because the sulphur at the α-phosphate interferes with some enzymatic functions but not others, modification of one end of a DNA molecule with the analog makes the end inert to specific processes such as exonuclease III digestion.

Other nucleotide analogs such as the dideoxynucleotides, when incorporated into DNA fragments, have also been shown to inhibit the 3'-5' exonuclease activity of DNA polymerase (Aktinson, M. R., et al. Biochem. 8:4897-4904 (1969)). These analogs are used extensively in the chain termination method of DNA sequencing because once inserted they prevent incorporation of additional nucleotides. Unlike the dNTP(αS), the dideoxynucleotides are unattractive for use in asymmetrically blocking digestion of DNA fragments. Because they lack the 3' hydroxyl group, fragments with terminal dideoxynucleotides are inert to ligation. Consequently, although double stranded fragments containing dideoxynucleotides can be asymmetrically digested, they cannot be made viable for in vivo functions.

A major use of the thionucleotides is the ability to generate single stranded DNA from a double stranded fragment. Single stranded DNA of fixed length is useful for several purposes including DNA sequencing by the chain termination technique (Sanger, F., et al. Proc. Nat'l. Acad. Sci. 74:5463-67 (1977)), S1 nuclease mapping of RNA transcripts (Weaver, R. F. Weismann C. Nucl. Acid Res. 7:1175-1193 (1979)), and site directed mutagenesis (Green, C. Tibbets C. Proc. Nat'l. Acad. Sci. 77:2455-2459 (1980)). When an α-thionucleotide is inserted into only one end of a fragment, limit digestion with exonuclease III destroys only the complementary strand. Such treatment provides a full length single strand and, if the complementary strand is desired, it can be obtained by appropriate choice of a restriction site at the other end of the fragment and of the α-thionucleotide used for the filling in reaction. Unlike other methods currently used for generating single strands (e.g., gel electrophoresis strand separation), the thio nucleotide procedure creates intact single strands regardless of length or sequence.

Most importantly, DNA containing the thio analog is replicated in vivo and, therefore, plasmids modified with this analog are competent for cellular transformation. Since all four dNTP(αS) will function similarly in regard to the instant invention, only the dATPα-S is exemplified herein.

Figure 9:
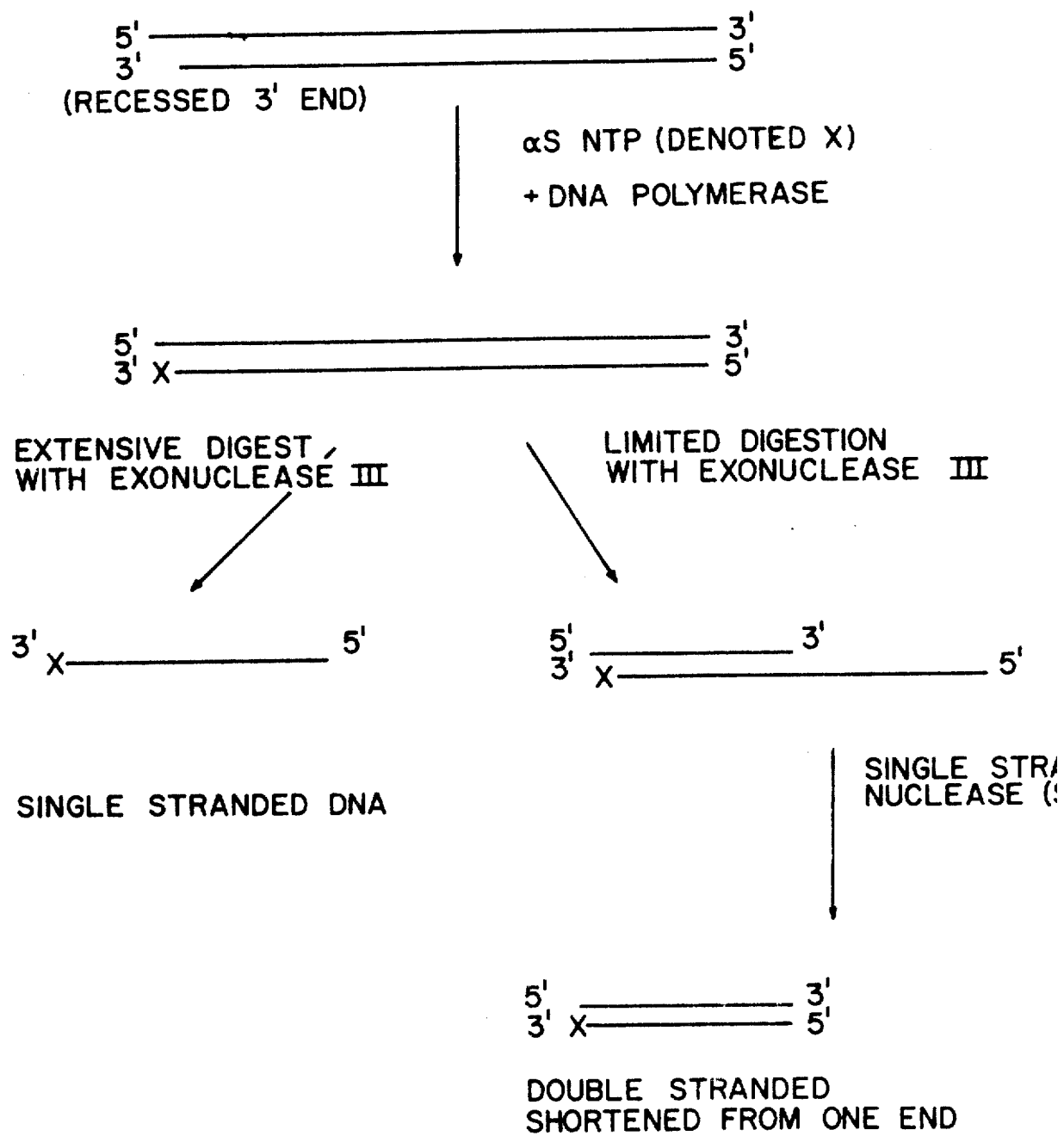
FIG. 9 illustrates two embodiments of the subject invention.

The two particular embodiments described above may be summarized by reference to FIG. 9.

A part of the substance of this invention has been described in a recent publication (S. D. Putney, et al. Proc. Nat'l. Acad. Sci 78(12): 7350–54 (1981)). This publication is hereby incorporated into the present disclosure and made part thereof.

The following examples are provided to illustrate, but not limit the scope of the instant invention.

EXAMPLE I

This example demonstrates the effectivenes of dATPαS in inhibiting the action of exonuclease III.

To show that the presence of dAMP(αS) within one strand of a double stranded fragment renders that strand resistant to exonuclease III digestion, a 302 bp fragment of known sequence, with a Bst EII generated end at one side and KpnI generated end at the other, was treated with DNA polymerase I, dCTP, dGTP, ($\alpha^{32}$P)dTTP, and either dATP(αS) or dATP (FIG. 1a).

The BstI II-Kpn I fragment was obtained by digesting the E. coli plasmid pSP201 with Bst EII and Kpn I and electrophoresing the products through a 5% polyacrylamide gel as described by Maniatis, et al. (Bio. Chem. 14:3787-94 (1975). The DNA was visualized by UV shadowing and isolated from the gel following the method Maxam & Gilbert (Meth. of Enz. GT:499–560 (1980).

Plasmid PSP201 (which contains the 302 base pair Bst EII-Kpn I fragment) was replicated, in E. coli. host KL386. Isolation and purification were performed by cleared lysate followed by cesium chloride centrifugation as described by Hockman (Cell 17:583–595 (1979)).

The dATP(αS) Sp diastereomer was prepared using the methods discussed in Byrant F. N. & Benkovic S. J. (Biochem. 18:2825-2828 (1979)). Because Bst EII leaves the 5' strand protruding, and Kpn I leaves the 3' end protruding, dAMP(αS) was inserted at only the 3' end of the Bst EII side of the fragment. Because ($\alpha$-$^{32}$P)TTP was included as a substrate, the fragments were labeled selectively at the Bst EII side and dAMP(αS) was positioned between the end of the fragment and the labeled dTMP. Due to the 3'-exonuclease activity of DNA polymerase I, the 3'-protruding strand of the Kpn I side was rendered flush. The result of this treatment was, therefore, a blunt ended fragment with dAMP(αS) located one nucleotide from one end.

The filling in reaction was done by incubating 1.5 g DNA for 30' at 18° C. with 50 mM Tris-HCl, pH 8.0, 5 mM MgCl$_2$, 10 mM 2-mercaptoethanol, 50 μM dGTP and dCTP, 10 μM α-$^{32}$P)dTTP, 50 μM dATP(αS) or dATP and 0.75 units of the large fragment of DNA polymerase (BRL). The products were purified by polyacrylamide electrophoresis as described by Maniatis, et al. (Biochem. 14:3787-94 (1975)). To perform the exonuclease III reactions, 0.005 g DNA was incubated in 6.6 mM Tris-HCl, pH 7.5, 6.6 mM MgCl$_2$, 6.6 mM 2-mercaptoethanol, 50 mM NaCl, and 1.12 units of exonuclease III (BRL) at 22° C. for the indicated times. The fragments were electrophoresed (6% polyacrylamide with 7 M urea) according to the method of Maxam and Gilbert (Methods Enzymol. 65:499–560 (1980)).

To verify that only one end of the fragment was labeled, it was restricted with Bst NI (which cleaves 157 base pairs from the Bst EII end (FIG. 1a)). This gave only one labeled fragment as visualized by electrophoresing the products through a denaturing polyacrylamide gel. Thus, the fragment was uniquely labeled and an experiment using the same fragment with dAMP replacing dAMP(αS) gave identical results.

The fragments were treated with a 1:9 molar ratio of DNA to exonuclease III. To monitor the extent of digestion, reaction products were electrophoresed through a denaturing gel which was subsequently autoradiographed. Because dAMP(αS) lies between the end of the fragment and the labeled dTMP (FIG. 1a), the fragment will remain labeled only if dAMP(αS) prevents removal of the labeled TMP by blocking exonuclease III digestion from this end of the molecule. On the other hand, loss of label should be rapid if dAMP-(αS) does not inhibit exonuclease III digestion.

The results are shown in FIG. 1b. Exonuclease III digestion was carried out for 0, 0.5, 2.0 and 8.0 minutes (lanes 1–4, respectively). Because the amount of radioactivity at each time point remains essentially unchanged, loss of label is clearly prevented by the terminal dAMP(αS). Identical digestions with the uncapped fragment revealed rapid loss of label (lanes 5–8).

Figure 2:
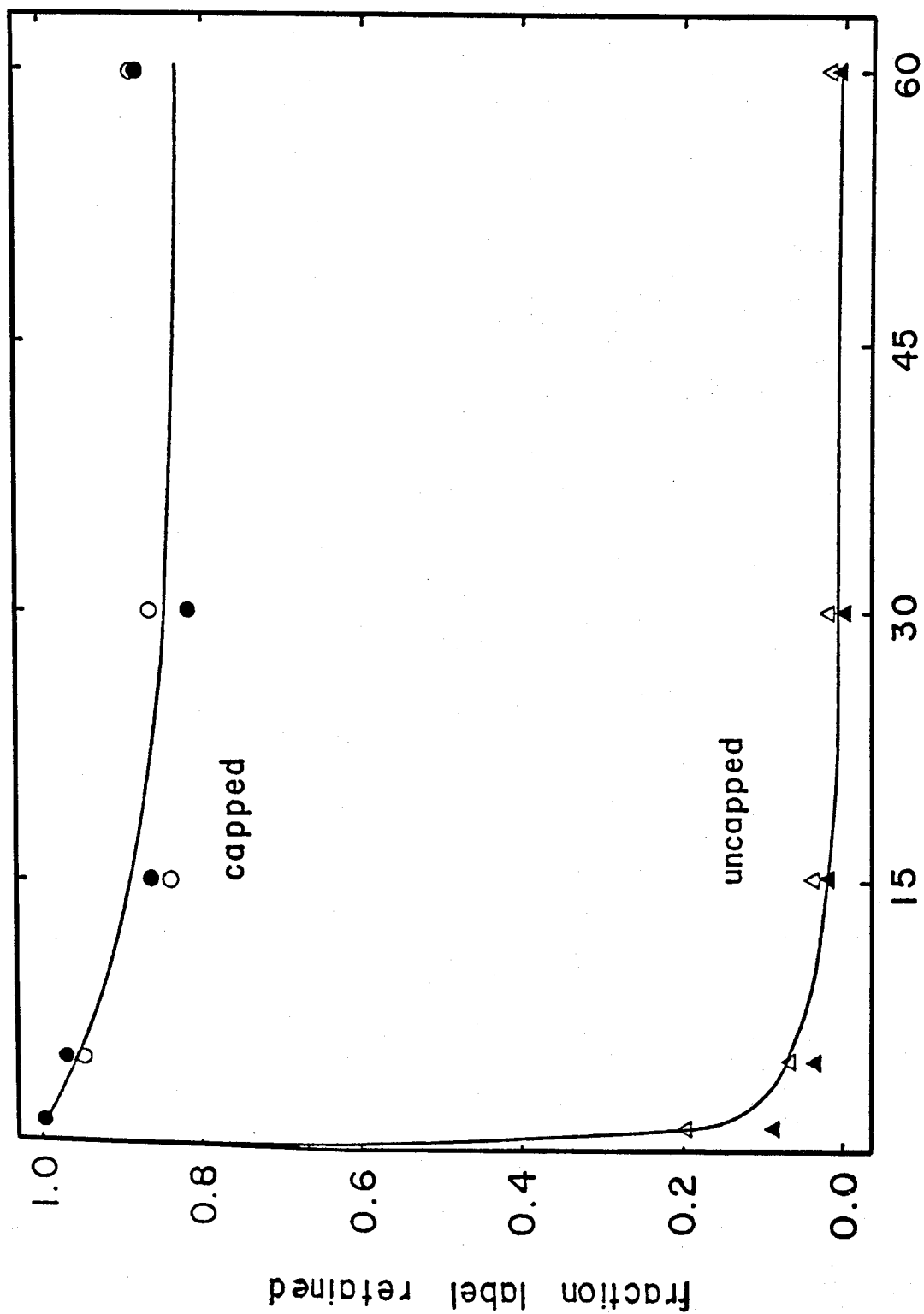
FIG. 2 shows the release of radioactive labelled phosphorous over time from Exonuclease III treated dAMPαS capped and uncapped DNA molecules.

The extent of resistance of capped fragments to exonuclease III was explored in another manner. A 5.3 kb fragment, with Bst EII 5'-overhang (FIG. 1) at both ends, was filled in with dCTP, dTTP, (α-$^{32}$P)dGTP, and either dATP(αS) or dATP. These fragments (labeled at both ends) were incubated with excess (0.2 mg of capped or uncapped fragment 12.5 units of enzyme) and the release of label was monitored by measuring TCA precipitable radioactivity. The results (FIG. 2) show that, at both 22° and 37° C., the amount of radioactivity in the capped fragment is almost unchanged during the duration of the reaction (60 min.) while the label is rapidly lost (1 min.) from the uncapped fragment. Thus, a single dAMP(αS) protects the end of a DNA fragment from prolonged exonuclease III digestion.

EXAMPLE II

This example illustrates the generation of full length single stranded DNA from a double stranded DNA sample.

Figure 3:
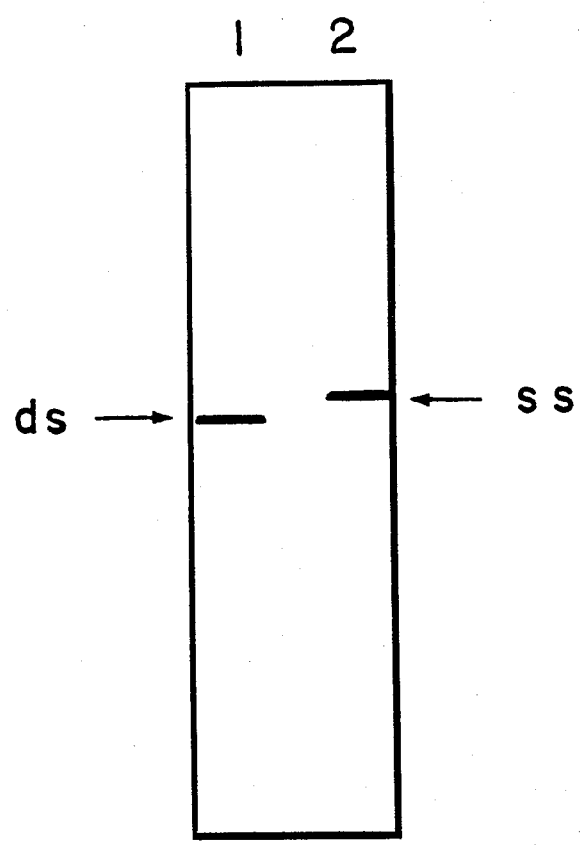
FIG. 3 represents an electrophoretic gel pattern of single and double stranded DNA molecules.

A 130 bp fragment, produced by Dde I (5' overhang) and Pvu I (3' overhang) cleavages, was filled in at the Dde I end with dAMP(αS) as in Example I. FIG. 3 shows the results of exonuclease III digestion of the 130 bp Dde I-Pvu I fragment containing dAMP(αS) at one end. Lane 1 shows 0.016 μg of undigested fragment and lane 2 contains 0.040 μg treated with 200 units exonuclease III per μg. Exonuclease III digestion produces single stranded DNA which migrates above the double strands. Electrophoresis was through a 7.5% polyacrylamide gel and the DNA was visualized with ethidium bromide staining. In an identical experiment using uncapped fragment, no DNA was visible after exonuclease III digestion.

EXAMPLE III

This example illustrates the unimpaired ability to perform routine recombinant DNA procedures employing DNA fragments containing dNTPαS.

Figure 4A:
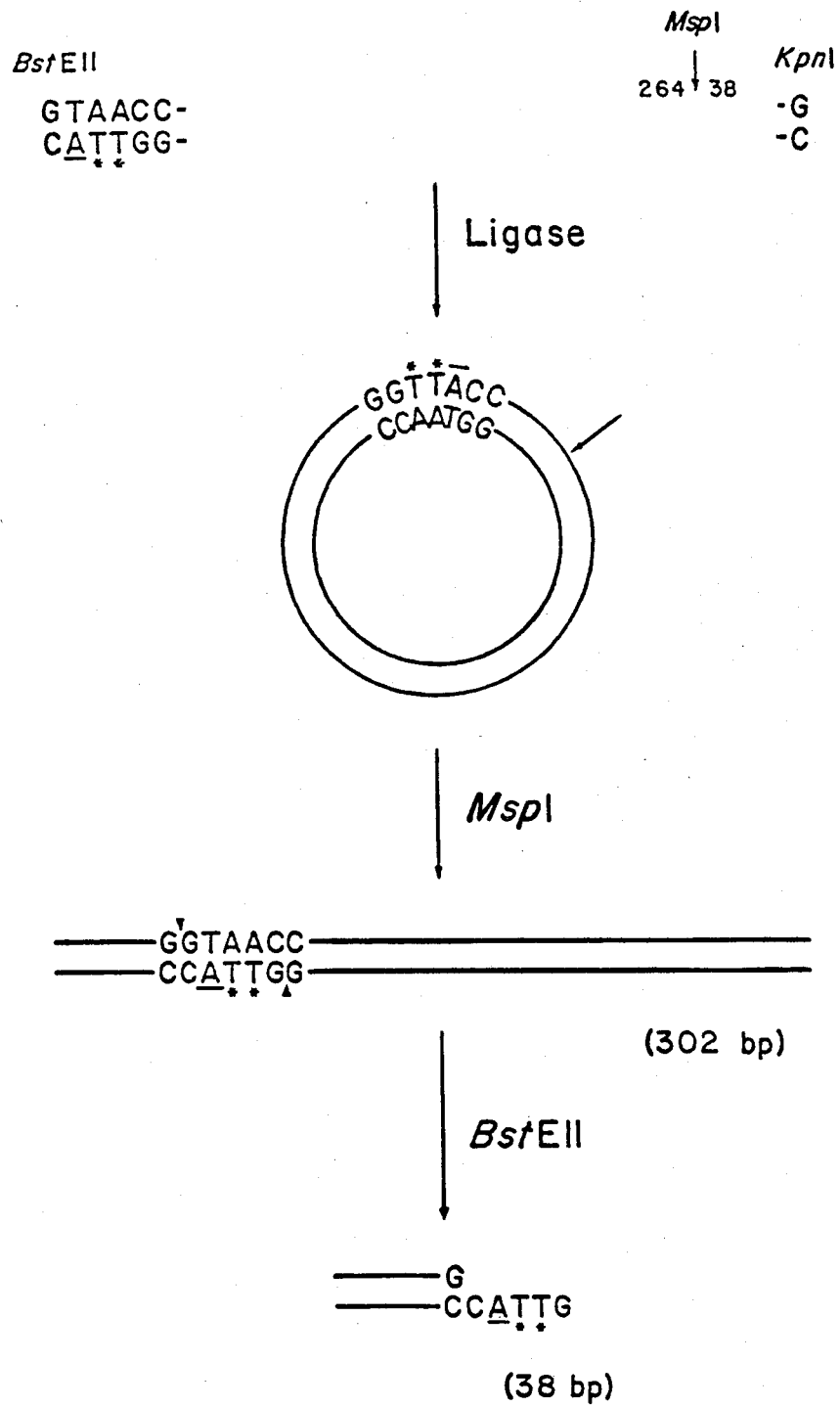
FIG. 4a illustrates the ligation and restriction of a dAMPαS capped DNA fragment.
Figure 4B:
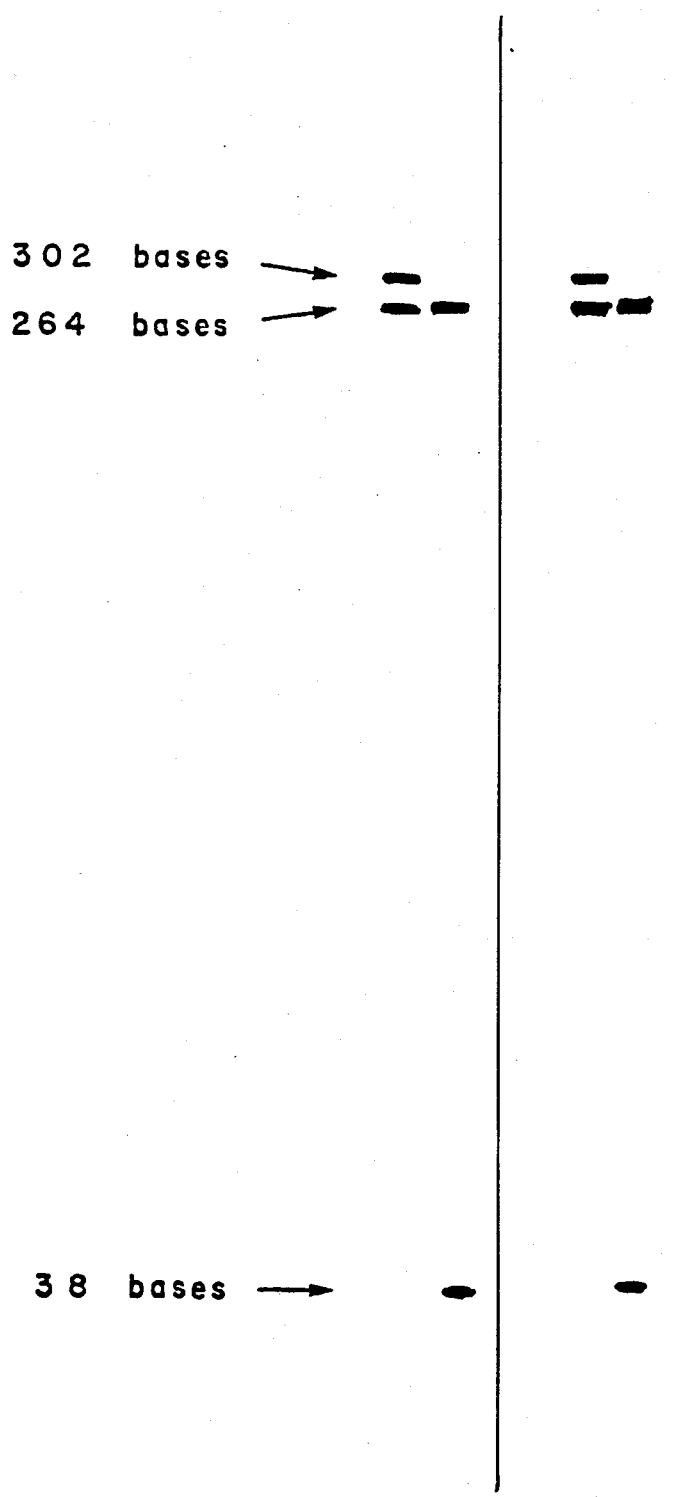
FIG. 4b represents an electrophorectic gel pattern of fragments of DNA after treatment with restriction enzymes Msp I and Bst EII.

The dAMP(αS) containing Bst EII-Kpn I fragment and the uncapped fragment (from Example I) were incubated separately with T4 DNA ligase under conditions which promote intramolecular flush end litigation. As shown in FIG. 4a (wherein the label is indicated by an asterisk and the dAMP(αS) is underlined), such a ligation joins the Bst EII and Kpn I ends. To assay the extent of ligation, the products were restricted with Msp I which cleaves the fragment 38 pairs from the Kpn I end. Following restriction and electrophoresis through a denaturing gel, two *labeled* bands are observed for both the capped and uncapped fragment (FIG. 4b, lanes 1 and 3). One 302 bases in length, results from fragments which underwent ligation. The other, 264 bases, is unligated fragment. This experiment demonstrates that dAMP(αS), located only one nucleotide from the site of joining, has no significant effect on the efficiency of this ligation reaction. Ligation was performed with 0.006 μg DNA (at a concentration of 0.075 μg/ml) in 50 mM Tris-HCl, pH 7.8, 8.7 mM MgCl$_2$, 1.0 mM ATP with 1.5 units T4 DNA ligase (BRL) for 16 hours at 22° C. Products were analyzed using a 6% polyacrylamide gel with 7 M urea.

Fortuitously, when the fragments are circularized, the Bst EII restriction site is regenerated (see FIG. 4a). This offers a test of whether dAMP(αS) interferes with the recognition of a restriction endonuclease. When the Msp I treated ligation products were restricted with Bst EII and electrophoresed (FIG. 4b, lanes 2 and 4), the 302 bp fragment disappeared and a new fragment appeared at 38 bp. Hence, the presence of dAMP(αS) within the recognition site for this endonuclease does not affect cleavage.

EXAMPLE IV

This example illustrates the usefulness of the instant invention for the contraction of modified recombinant DNA reactors.

The role of plasmids in molecular cloning technology is well established. By the use of restriction endonucleases, fragments of DNA are generated that can be readily inserted into appropriately cleaved plasmids and then introduced into host cells. Plasmid pB322 a well-known plasmid of *E. coli* with a molecular weight of $2.7 \times 10^6$ daltons (4362 nucleotides) contains a single Pst I restriction site located with a gene coding for ampicillin resistance as well as single sites for Bam HI and Sal I with a gene for tetracycline resistance. There are also single sites for Eco RI, Hind III and Aua I.

Figure 5A:
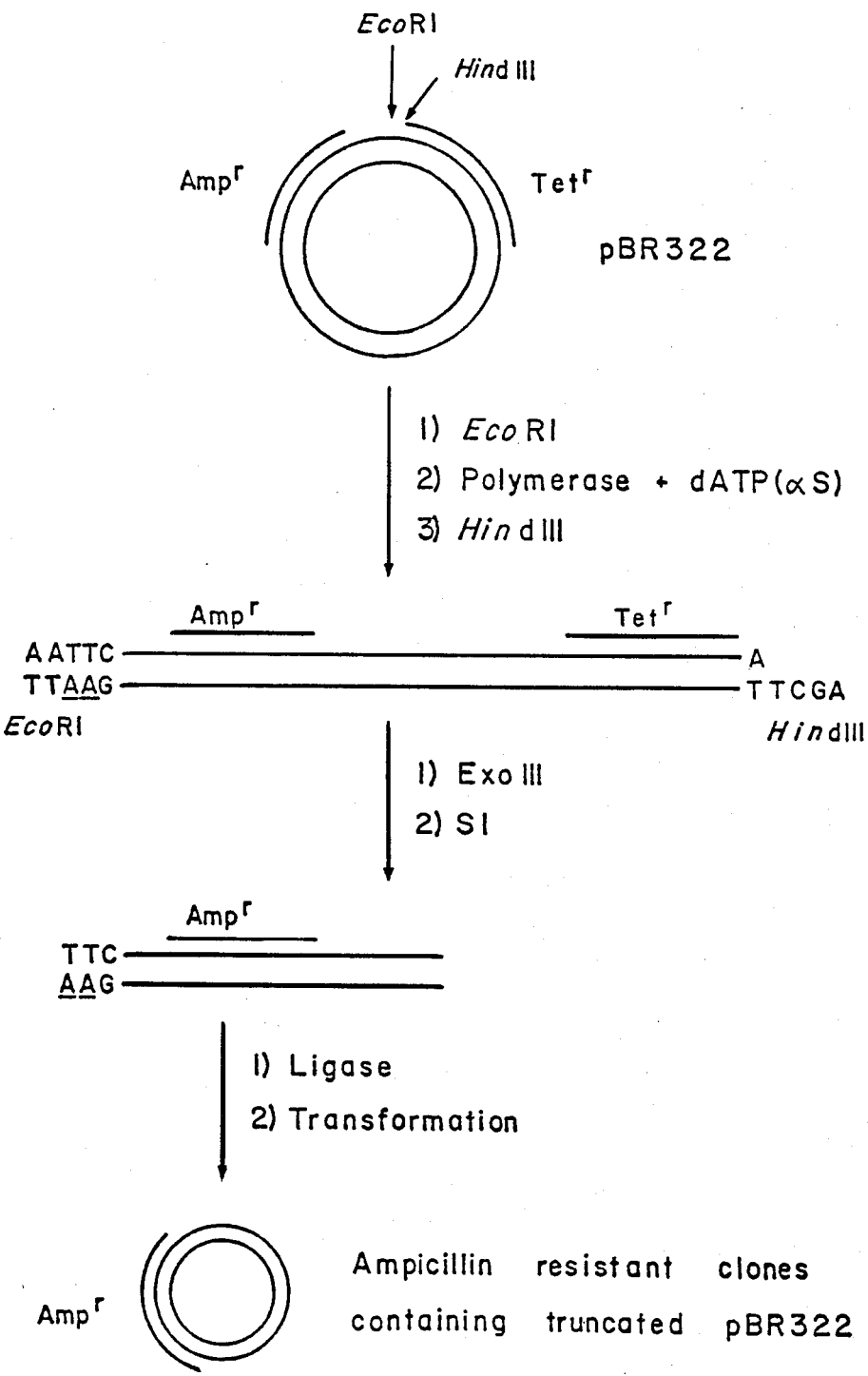
FIG. 5a illustrates the use of dATP(α-S) to construct a truncated form of plasmid pBR322.

The design of the experiment is outlined in FIG. 5a. pBR322 was opened at the unique Eco RI site and the recessed 3' ends were rendered flush with DNA polymerase in the presence of dATP(αS) and dTTP. Restriction was then performed with Hind III to generate a fragment with dAMP(αS) at one end. Limited exonuclease III treatment followed by S1 nuclease (to produce flush ends) resulted in forms of pBR322 which were shortened from the end which lacked dAMP(αS). This treatment destroyed the region conferring tetracycline resistance. The fragments were then ligated under conditions which promote recircularization, and an ampicillin/tetracycline sensitive host was transformed.

Selection was made either for ampicillin or for tetracycline resistance. No clones exhibiting tetracycline resistance were found, but many were isolated as ampicillin resistant. (A control experiment, where no exonuclease III treatment was performed, revealed that clones carrying pBR322 missing only the region between the Eco RI and Hind III sites are tetracycline resistant.) This suggests that, due to dAMP(αS) incorporation, exonuclease III digestion proceeded from the Hind III end and not from the Eco RI end.

Plasmid DNA was isolated from one ampicillin resistant/tetracycline sensitive clone to assess the nature and extent of exonuclease III treatment. Upon restriction with Pst I (which cuts pBR322 once within the Ap$^r$ region), it was found that the resulting plasmid was about 2.0 kb in length and therefore 2.4 kb had been removed by exonuclease III. Determination of the precise region removed by exonuclease III was made by restricting the truncated plasmid with Hae followed by subsequent electrophoresis of the products. Because Hae III cleaves pBR322 times identification of the Hae III sites present in the modified plasmid reveal the region missing from the original pBR322.

To generate the truncated plasmid, 2.0 μg of pBR322 were restricted with Eco RI and the fragment was incubated with dATP(αS), dTTP, and DNA Polymerase. After restriction with Hind III, the fragments were incubated with 20 units exonuclease III for 15' at 37° C. as in Example 1. Subsequent S1 nuclease treatment and ligation was performed essentially as described in Roberts, T. M. and Laver G. D. (Meth. of Enz. 68:473–82 (1980)). The DNA was then used to transform cell strain KL386 according to the procedure of Theall, et al. (Molec. Gen. Genets. 156:221–227 (1977)). Selection was made for either ampicillin or tetracycline resistance. While no clonies grew on tetracycline, 40 were percent on ampicillin. From one of these, plasmid was isolated and 0.3 g was digested with Hae III and electrophoresed in parallel with Hae III digested pBR322 on a 7.5% polyacrylamide gel.

Figure 5B:
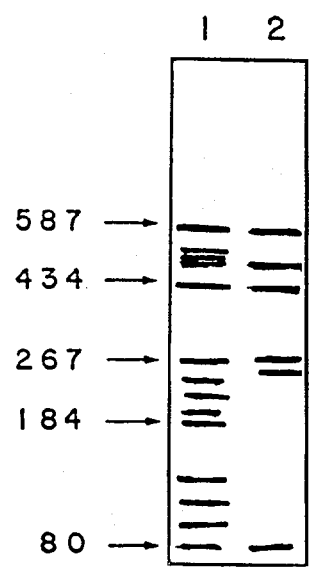
FIG. 5b represents an electrophoretic gel pattern of DNA fragments of PB322 and truncated pBR322 after digestion with endonuclease Hae III.
Figure 6:
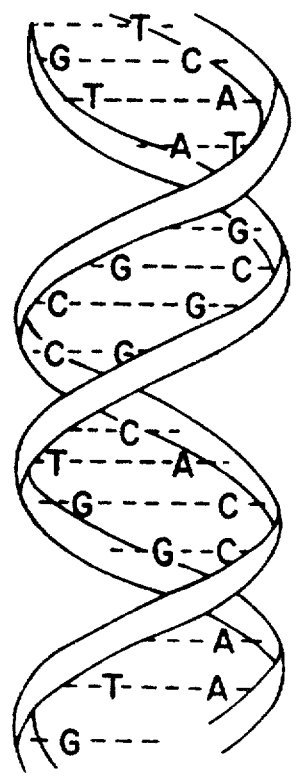
FIG. 6 illustrates the double-stranded structure of DNA.

The results of Hae III digestion of intact pBR322, in parallel with those of the shortened plasmid, are shown in FIG. 5b, lanes 1 and 2. All fragments produced from Hae III cleavages within the region from nucleotide 174 to 1949 in pBR322 are missing from the truncated plasmid, while all other fragments are present. Hae III cleavage of the truncated plasmid generates a fragment of approximate length 250, which is not present in the pBR322 digest. Based on the lengths of the fragments produced, it is estimated that the plasmid has a length of 2120 nucleotides which means that the exonuclease III digest proceeded to approximately 160 bases from the origin of replication. Particularly important is the presence in the truncated plasmid of the Hae III site at position 4344, which is only 18 nucleotides from the original Eco RI site. Another point is that the in vitro ligation preceeded even though the dAMP(αS) was at the very end of the fragment. This confirms data in Example 3 and shows that ligation is not affected by thio analog.

We claim:

1. A method for the asymmetric degradation of DNA comprising
   (a) generating DNA fragments by the application of restriction endonucleases
   (b) end-blocking one terminus of each of said fragments by the introduction of a thionucleotide analog protecting group said protecting group being capable of inhibiting exonuclease activity
   (c) specifically degrading the non-protected terminus of said end-blocked fragment by the application of exonucleases.

2. A method of claim 1 wherein said restriction endonucleases comprise endonucleases which generate recessed 3' termini as a result of their activity in combination with an endonuclease that generates recessed 5' termini or flush ended termini.

3. A method of claim 2 wherein said recessed 3' termini generating endonucleases are selected from the group consisting of Ava I, Ava II, Bam HI, Bcl I, Bgl II, Bst EII, Dde I, Eco RI, Eco RII, Hind III, Hinf I, Hpa II, Mbo I, Sal I, Sau 3A, Sau 96I, Taq I, Xba I and Xho I.

4. A method of claim 2 wherein said recessed 5' termini generating endonucleases are selected from the group consisting of Bgl I, Cfo I, Dpn I, Hae II, Hha I, Pst I, Pvu I, Kpn I, Sph I, Sst I, Sst II and Xor II.

5. A method of claim 2 wherein said flush termini generating endonucleases are selected from the group consisting of Alu I, Bal I, Hae III, Hpa I, Mbo II, Pvu II, Sma I and Tha I.

6. A method of claim 2 wherein said recessed 3' termini generating endonuclease is Dde I and said recessed 5' termini generating endonuclease is Pvu I.

7. A method of claim 1 wherein said thionucleotide analogs are nucleotide thiotriphosphates.

8. A method of claim 7 wherein said thionucleotide analogs are selected from the group of Sp diasteromers consisting of 2' deoxyadenosine 5'-O-(1-thiotriphosphate), 2' deoxyguanosine 5'-O-(1-thiotriphosphate, 2' deoxythymidine 5'-O-(1-thiotriphosphate) and 2' deoxycytidine 5'-O-(1-thiotriphosphate).

9. A method of claim 8 wherein said thionucleotide analog is deoxyadenosine 5'-O-(1-thiotriphosphate).

10. A method of claim 1 wherein said thionucleotide analogs are introduced on to the recessed 3'-termini by the treatment with DNA polymerase I.

11. A method of claim 1 wherein said non-protected terminus is degraded by the action of Exonuclease III.

12. A method for the asymmetric degradation of DNA comprising
  (a) generating DNA fragments with one recessed 3'OH terminus by the application of restriction endonucleases
  (b) end-blocking said recessed terminus by the introduction of a thionucleotide protecting group said protecting group being capable of inhibiting exonuclease activity
  (c) specifically degrading the non-protected terminus of said end-blocked fragment by the application of exonucleases.

13. A method of claim 12 wherein said restriction endonucleases comprise endonucleases which generate recessed 3' termini as a result of their activity in combination with an endonuclease that generates recessed 5' termini or flush ended termini.

14. A method of claim 13 wherein said recessed 3' termini generating endonucleases are selected from the group consisting of Ava I, Ava II, Bam HI, Bcl I, Bgl II, Bst EII, Dde I, Eco RI, Eco RII, Hind III, Hinf I, Hpa II, Mbo I, Sal I, Sau 3A, Sau 96I, Taq I, Xha I and Xho I.

15. A method of claim 13 wherein said recessed 5' termini generating endonucleases are selected from the group consisting of Bgl I, Cfo I, Dpn I, Hae II, Hha I, Pst I, Pvu I, Kpn I Sph I, Sst I, Sst II and Xor II.

16. A method of claim 13 wherein said flush termini generating endonucleases are selected from the group consisting of Alu I, Bal I, Hae III, Hpa I, Mbo II, Pvu II, Sma I and Tha I.

17. A method of claim 13 wherein said recessed 3'termini generating endonuclease is Dde I and said recessed 5'termini generating endonuclease is Pvu I.

18. A method of claim 12 wherein said thionucleotides are analogs selected from the group consisting of Sp diasteromers comprising 2' deoxyadenosine 5'-O-(1-thiotriphosphate), 2' deoxyguanosine 5'-O-(1-thiotriphosphate), 2' deoxythymidine 5'-O-(1-thiotriphosphate) and 2' deoxycytidine 5'-O-(1-thiotriphosphate).

19. A method of claim 18 wherein said thionucleatide analog is deoxyadenosine 5'-O-(1-thiotriphosphate).

20. A method of claim 12 wherein said thionucleotides are introduced on to the recessed 3' termini by the treatment with DNA polymerase.

21. A method of claim 12 wherein said non-protected terminus is degraded by the action of Exonuclease III.

22. A method for the generation of single strands of DNA from double stranded DNA comprising.
  (a) generating DNA fragments by the application of restriction endonucleases Dde I and Pvu I,
  (b) end blocking the Dde I generated terminus by the introduction of 2' deoxyadenosine 5'-O-(1-thiotriphosphate) by treatment with DNA polymerase I,
  (c) degrading the strands containing the unprotected 3' termini with Exonuclease III for a sufficient period of time to effect the complete degradation of said strand,
  (d) recovering the remaining single strand of DNA.

23. A method for the controlled degradation of DNA from one end of the molecule comprising
  (a) generating DNA fragments by the application of restriction endonucleases Dde I and Pvu I,
  (b) end-blocking the Dde I generated terminus by the introduction of 2'-deoxyadenosine-5-O-(1-thiotriphosphate) by treatment with DNA polymerase I,
  (c) partially degrading the strand coating the unprotected 3' terminus with Exonuclease III by incubating a fraction of the time necessary to completely degrade the chain, terminating the Exonuclease III degradation, degrading the resultant 5' single strand and with nuclease S1 thereby reducing the length of said DNA fragment from a specific termini in a controlled fashion.

24. In a method for the sequencing of DNA wherein chain growth is terminated the improvement comprising generating single stranded DNA of fixed length by:
  (a) generating DNA fragments by the application of restriction endonucleases Dde I and Pvu I,
  (b) end blocking the Dde I generated terminus by introduction of 2' deoxyadenosine 5'-O-(1-thiotriphosphate) by treatment with DNA polymerase I,
  (c) degrading the strands containing the unprotected 3' termini with Exonuclease III for a sufficient period of time to effect the complete degradation of said strand,
  (d) recovering the remaining single strand of DNA.

25. In a method for the S1 nuclease mapping of RNA transcripts wherein single stranded DNA is hybridized to RNA the improvement comprising the generating of single stranded DNA of fixed length by:
  (a) generating DNA fragments by the application of restriction endonucleases Dde I and Pvu I,
  (b) end blocking the Dde I generated terminus by introduction of 2' deoxyadenosine 5'-O-(1-thiotriphosphate) by treatment with DNA polymerase I,
  (c) degrading the strands containing the unprotected 3' termini with Exonuclease III for a sufficient period of time to effect the complete degradation of said strand,
  (d) recovering the remaining single strand of DNA.

26. In a method of site directed in vitro mutagenesis wherein partially denatured double stranded DNA is incubated with single stranded DNA the improvement comprising the generating of single stranded DNA of fixed length by:
(a) generating DNA fragment by the application of restriction endonucleases Dde I and Pvu I,
(b) end blocking the Dde I generated terminus by introduction of 2' deoxyadenosine 5'-O-(1-thiotriphosphate) by treatment with DNA polymerase I,
(c) degrading the strands containing the unprotected 3' termini with Exonuclease III for a sufficient period of time to effect the complete degradation of said strand,
(d) recovering the remaining single strand of DNA.

27. The method of claim 11 followed by degradation by S1 nuclease.

28. The method of claim 21 followed by degradation by S1 nuclease.

* * * * *

UNITED STATES PATENT OFFICE
CERTIFICATE OF CORRECTION

Patent No. 4,521,509    Dated June 4, 1985

Inventor(s) Stephen J. Benkovic, et al.

It is certified that error appears in the above-identified patent and that said Letters Patent are hereby corrected as shown below:

IN THE DRAWINGS:

Add Figures 6 - 9, as attached.

Signed and Sealed this

First Day of October 1985

[SEAL]

Attest:

Attesting Officer

DONALD J. QUIGG

Commissioner of Patents and Trademarks—Designate

```
5'————CTNAG————3'

3'————GANTC————5'
```
WHERE N= ANY OF THE FOUR BASES

```
5' TNAG————3'

3'
  OH C————5"
```

FIG. 8A

```
5' TNAG————————3'

3' ⒶNTC————————5''''
```

FIG. 8B